United States Patent
Biyani et al.

(10) Patent No.: US 8,343,201 B2
(45) Date of Patent: Jan. 1, 2013

(54) PEDICLE SCREW ASSEMBLY HAVING A RETRACTABLE SCREW TIP FOR FACILITATING THE SECUREMENT OF THE PEDICLE SCREW ASSEMBLY TO A SPINAL VERTEBRA

(75) Inventors: Ashok Biyani, Sylvania, OH (US); Gary Durivage, Graytown, OH (US)

(73) Assignee: The University of Toledo, Toledo, OH (US)

( * ) Notice: Subject to any disclaimer, the term of this patent is extended or adjusted under 35 U.S.C. 154(b) by 470 days.

(21) Appl. No.: 12/535,026

(22) Filed: Aug. 4, 2009

(65) Prior Publication Data
US 2010/0298892 A1  Nov. 25, 2010

Related U.S. Application Data

(60) Provisional application No. 61/086,447, filed on Aug. 5, 2008.

(51) Int. Cl.
*A61B 17/04* (2006.01)
*A61B 17/86* (2006.01)
*A61F 2/08* (2006.01)

(52) U.S. Cl. ......... 606/318; 606/309; 606/320; 606/328

(58) Field of Classification Search .................. 606/286, 606/318, 328, 309–312, 320; 433/383, 395
See application file for complete search history.

(56) References Cited

U.S. PATENT DOCUMENTS

| | | | |
|---|---|---|---|
| 4,940,467 A | 7/1990 | Tronzo | |
| 5,209,753 A | 5/1993 | Biedermann et al. | |
| 5,354,299 A | 10/1994 | Coleman | |
| 2004/0147929 A1* | 7/2004 | Biedermann et al. | 606/61 |
| 2004/0210227 A1* | 10/2004 | Trail et al. | 606/73 |
| 2005/0038438 A1 | 2/2005 | Anderson et al. | |
| 2006/0079903 A1 | 4/2006 | Wong | |
| 2006/0106390 A1* | 5/2006 | Jensen et al. | 606/73 |
| 2006/0111712 A1 | 5/2006 | Jackson | |
| 2007/0213732 A1 | 9/2007 | Khanna et al. | |
| 2009/0005822 A1* | 1/2009 | Kitchens | 606/86 B |
| 2009/0187194 A1 | 7/2009 | Hamada | |
| 2009/0187220 A1 | 7/2009 | Hamada | |

* cited by examiner

FOREIGN PATENT DOCUMENTS

WO    WO2009091616 A2    7/2009

OTHER PUBLICATIONS

International Search Report and Written Opinion, Application No. PCT/US09/52653, Dated Mar. 21, 2012.

*Primary Examiner* — Andrew Yang
*Assistant Examiner* — Olivia C Chang
(74) *Attorney, Agent, or Firm* — MacMillan, Sobanski & Todd, LLC

(57) ABSTRACT

A pedicle screw assembly has a retractable screw tip that facilitates the securement of the pedicle screw assembly to a spinal vertebra in a minimally invasive fashion during an orthopedic surgical procedure. The pedicle screw assembly includes a body portion including a head and a shank. The shank includes an outer surface with a thread provided thereon, an end having a cutting tip provided thereon, and a bore extending inwardly from the end and having an internally threaded region provided therein. The pedicle screw assembly also includes a tip portion including a body having a cutting edge and a shank extending from the body. The shank has an externally threaded region provided thereon that cooperates with the internally threaded region of the bore to permit movement of the tip portion relative to the body portion between extended and retracted positions.

10 Claims, 9 Drawing Sheets

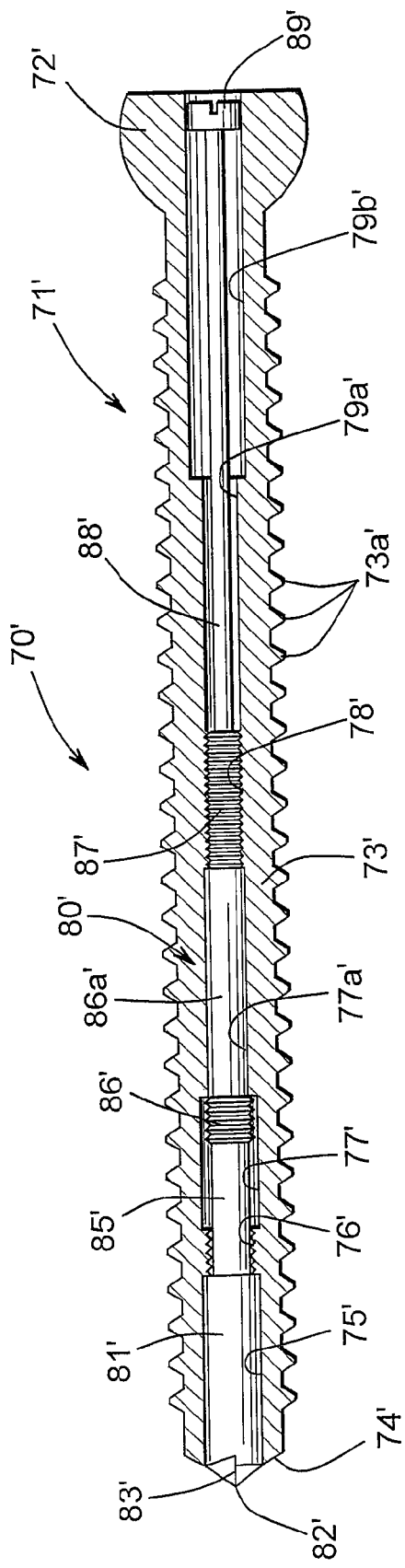
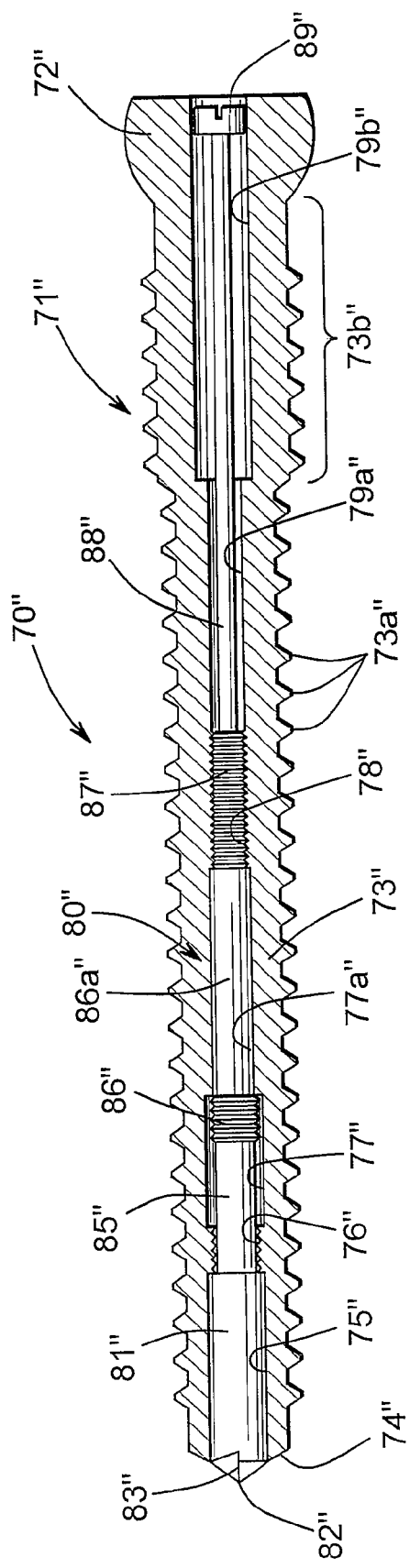
FIG. 14
FIG. 15

PEDICLE SCREW ASSEMBLY HAVING A RETRACTABLE SCREW TIP FOR FACILITATING THE SECUREMENT OF THE PEDICLE SCREW ASSEMBLY TO A SPINAL VERTEBRA

CROSS-REFERENCE TO RELATED APPLICATIONS

This application claims the benefit of U.S. Provisional Application No. 61/086,447, filed Aug. 5, 2008, the disclosure of which is incorporated herein by reference.

STATEMENT REGARDING FEDERALLY SPONSORED RESEARCH OR DEVELOPMENT

Not applicable.

BACKGROUND OF THE INVENTION

This invention relates in general to fasteners that are used to secure devices to bones in surgical procedures. In particular, this invention relates to a pedicle screw assembly having a retractable screw tip that facilitates the securement of the pedicle screw assembly to a spinal vertebra in a minimally invasive fashion during an orthopedic surgical procedure.

Many surgical procedures involve the securement of a device to a bone. For example, during an orthopedic surgical procedure, it is often necessary to secure a support or alignment device to one or more vertebrae in the lumbar or thoracic region of the spine. The securement of such a device to the vertebra usually involves a series of relatively complex steps. For example, in one known procedure, a conventional Jamshidi needle (which includes a hollow outer cannula and an inner obturator having a tapered cutting edge) is initially inserted through a relatively small incision until the tapered cutting edge of the obturator engages a desired location on the surface of the vertebra where a fastener, such as a pedicle screw, is to be secured. The precise location where the tapered cutting edge of the obturator engages the surface of the vertebra is usually determined using conventional fluoroscopic or other imaging or navigational techniques.

Once the tapered cutting edge of the obturator has been positioned at the desired location on the surface of the vertebra, a conventional impaction tool is used to advance the Jamshidi needle further within the vertebra so as to create a passageway therein. The depth of the insertion of the Jamshidi needle within the vertebra can be determined using conventional fluoroscopic or other imaging or navigational techniques. Then, the obturator is removed from the Jamshidi needle, leaving behind the hollow outer cannula. A flexible guide wire is next inserted through the hollow outer cannula of the Jamshidi needle until the leading end thereof extends through the passageway and is received within the body of the vertebra at a desired depth. The depth of the insertion of the leading end of the guide wire within the body of the vertebra can be determined using conventional fluoroscopic or other imaging or navigational techniques. Then, the hollow outer cannula of the Jamshidi needle is withdrawn from the vertebra, leaving the leading end of the guide wire within the body of the vertebra.

A conventional cannulated threading tool is next inserted over the trailing end of the guide wire and guided therealong to the relatively short passageway in the vertebra. The threading tool is used to tap a thread within the passageway in the vertebra. The depth of the thread that is tapped within the passageway can be determined using conventional fluoroscopic or other imaging or navigational techniques. Next, the threading tool is withdrawn, and a cannulated pedicle screw is inserted over the trailing end of the guide wire. The pedicle screw is guided along the guide wire until a threaded tip of the pedicle screw is guided to the tapped passageway in the vertebra, again using conventional fluoroscopic or other imaging or navigational techniques. The pedicle screw is secured to the vertebra by rotating it about the guide wire with a conventional tool, which causes the threaded tip of the pedicle screw to thread within the tapped passageway in the vertebra. Such rotation is continued until the pedicle screw has been driven a predetermined distance into the body of the vertebra that, again, can be determined using conventional fluoroscopic or other imaging or navigational techniques. Lastly, the guide wire is removed, leaving the pedicle screw secured to the vertebra, to which the support or alignment device can be secured.

Although this procedure for securing a conventional pedicle screw to a vertebra has functioned satisfactorily, it can be seen that the fluoroscopic or other imaging or navigational techniques are frequently employed, which is time consuming and can result in significant radiation exposure. Thus, it would be desirable to provide an improved structure for a pedicle screw or similar fastener that avoids these issues.

SUMMARY OF THE INVENTION

This invention relates to a pedicle screw assembly having a retractable screw tip that facilitates the securement of the pedicle screw assembly to a spinal vertebra in a minimally invasive fashion during an orthopedic surgical procedure. The pedicle screw assembly includes a body portion including a head and a shank. The shank includes an outer surface with a thread provided thereon, an end having a cutting tip provided thereon, and a bore extending inwardly from the end and having an internally threaded region provided therein. The pedicle screw assembly also includes a tip portion including a body having a cutting edge and a shank extending from the body. The shank has an externally threaded region provided thereon that cooperates with the internally threaded region of the bore to permit movement of the tip portion relative to the body portion between extended and retracted positions.

Various aspects of this invention will become apparent to those skilled in the art from the following detailed description of the preferred embodiments, when read in light of the accompanying drawings.

BRIEF DESCRIPTION OF THE DRAWINGS

FIG. 14 is an assembled side elevational view, partially in cross section, of a fifth embodiment of a pedicle screw assembly in accordance with this invention.

FIG. 15 is an assembled side elevational view, partially in cross section, of a sixth embodiment of a pedicle screw assembly in accordance with this invention.

DETAILED DESCRIPTION OF THE PREFERRED EMBODIMENTS

Figure 1:
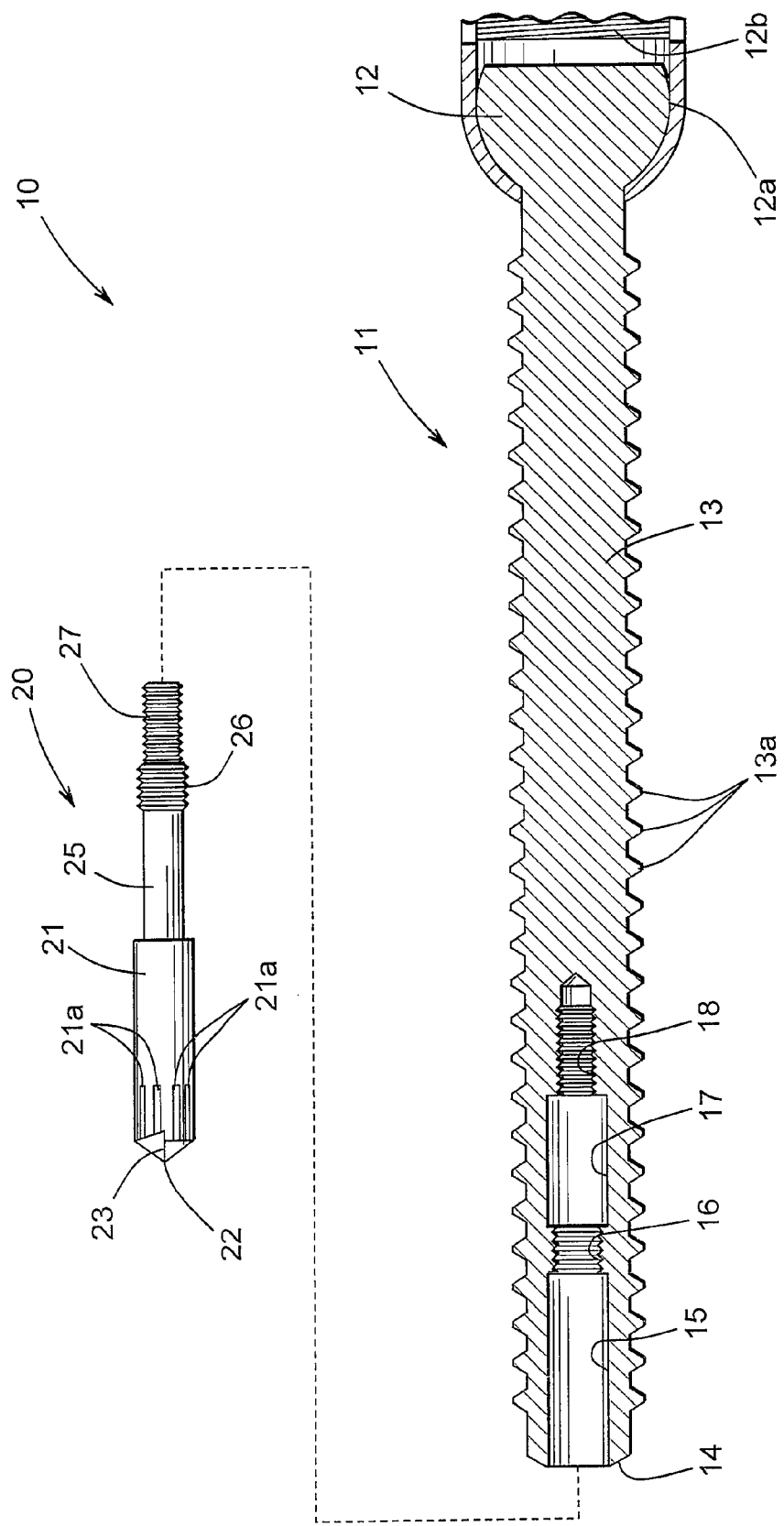
FIG. 1 is an exploded side elevational view, partially in cross section, of a first embodiment of a pedicle screw assembly including a tip portion and a body portion in accordance with this invention.

Referring now to the drawings, there is illustrated in FIGS. 1 through 4 a first embodiment of a pedicle screw assembly, indicated generally at 10, in accordance with this invention. As will be explained in detail below, the illustrated pedicle screw assembly 10 can be used to facilitate the securement of a device to a bone. However, the pedicle screw assembly 10 of this invention may be used for any desired purpose or in any desired surgical procedure.

The first embodiment of the pedicle screw assembly 10 includes a body portion, indicated generally at 11, having a head 12 provided at a first end thereof and an elongated shank 13 that extends from the head portion 12. The body portion 11 of the pedicle screw assembly 10 may be formed from any desired material, such as titanium, stainless steel, cobalt-chrome, or other medically-approved biomaterial. In the illustrated embodiment, the head 12 of the body portion 11 is generally semi-spherical in shape. However, the head 12 may be formed having any desired shape. A conventional tulip or yoke (a portion of which is shown at 12a) may be provided on the head 12 of the first embodiment of the pedicle screw assembly 10. Typically, the inner surface of the tulip 12a has an internal thread 12b provided thereon, the purpose of which will be described below. However, it will be appreciated that the head 12 and the tulip 12a of the pedicle screw assembly 10 may be formed having any desired structures. The illustrated semi-spherical head 12 and the associated tulip 12a function in the nature of a universal joint to provide a poly-axial pedicle screw assembly 10. If desired, the pedicle screw assembly 10 may be mono-axial, having a fixed or unidirectional head permitting movement along one axis only. The shank 13 of the body portion 11 has an outer surface that is provided with a helical or similar thread 13a. The purpose for this thread 13a will be explained below.

The body portion 11 of the first embodiment of the pedicle screw assembly 10 has a second end that terminates in a cutting tip 14. The cutting tip 14 may be embodied as any desired shape or structure (or combination of shapes or structures) that can remove bone material from a vertebra (not shown) when rotated relative thereto. The second end of the body portion 11 also has a bore provided therein that extends inwardly from the cutting tip 14. The illustrated bore is generally hollow and cylindrical in shape and includes a first non-threaded region 15, a relatively large diameter internally threaded region 16, a second non-threaded region 17, and a relatively small diameter internally threaded region 18. The purposes for each of these regions 15 through 18 of the bore will be explained below.

The first embodiment of the pedicle screw assembly 10 also includes a tip portion, indicated generally at 20. The tip portion 20 of the first embodiment of the pedicle screw assembly 10 may also be formed from any desired material, such as titanium, stainless steel, cobalt-chrome, or other medically-approved biomaterial. In this first embodiment of the pedicle screw assembly 10, the tip portion 20 is embodied as a self-drilling tip having a body 21 that includes a drill tip cutting edge 22 and a clearance cutting edge 23. An elongated shank 25 extends from the body 21 and has both a relatively large diameter externally threaded region 26 and a relatively small diameter externally threaded region 27 provided thereon. The purposes for each of these structures and regions 22 through 27 of the tip portion 20 will also be explained below.

If desired, the outer surface of the body 21 may be formed having a non-circular cross-sectional shape. As shown in FIG. 1, this non-circular cross-sectional shape may be embodied as one or more grooves 21a (shown only in FIG. 1) that extend outwardly from the outer surface of the body 21. Alternatively, this non-circular cross-sectional shape may be embodied as one or more projections, ridges, or any other structure or combination of structures provided the outer surface of the body 21. Additionally, this non-circular cross-sectional shape may be inherent in the cross-sectional shape of the body 21, which may be rectangular, oval, or any other non-circular cross-sectional shape. The purpose for this non-circular cross-sectional shape will be explained below.

Figure 2:
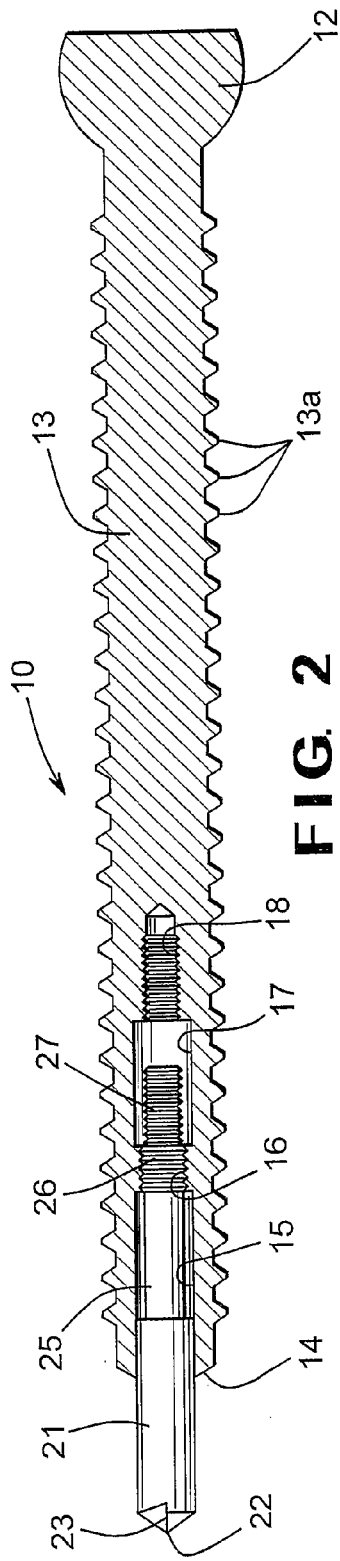
FIG. 2 is an assembled side elevational view, partially in cross section, of the first embodiment of the pedicle screw assembly illustrated in FIG. 1, wherein the tip portion is shown in an extended position relative to the body portion.

Referring now to FIG. 2, the first embodiment of the pedicle screw assembly 10 is assembled by initially inserting the elongated shank 25 of the tip portion 20 within the bore provided in the second end of the body portion 11. The outer diameters defined by the relatively large externally threaded region 26 and the relatively small externally threaded region 27 of the tip portion 20 are preferably both smaller than the inner diameter defined by the first non-threaded region 15 of the bore provided in the second end of the body portion 11. Thus, the relatively large externally threaded region 26 and the relatively small externally threaded region 27 of the tip portion 20 both pass freely through the first non-threaded region 15 of the bore as the tip portion 20 is initially inserted within the bore. However, the outer diameter defined by the body 21 of the tip portion 20 is preferably sized such that it is journaled on the first non-threaded region 15 concentrically within the bore for free sliding movement relative thereto.

The outer diameter defined by the relatively small externally threaded region 27 of the tip portion 20 is also preferably somewhat smaller than the inner diameter defined by the relatively large internally threaded region 16 of the bore provided in the second end of the body portion 11. Thus, as the elongated shank 25 of the tip portion 20 is continued to be inserted within the bore provided in the second end of the body portion 11, the relatively small externally threaded region 27 of the tip portion 20 passes freely through the relatively large internally threaded region 16 of the bore provided in the second end of the body portion 11.

However, the outer diameter defined by the relatively large externally threaded region 26 of the tip portion 20 is approximately the same as the inner diameter defined by the relatively large internally threaded region 16 of the bore provided in the second end of the body portion 11. Thus, as shown FIG. 2, the relatively large externally threaded region 26 of the tip portion 20 will engage the relatively large internally threaded region 16 of the bore provided in the second end of the body portion 11. Thereafter, rotation of the tip portion 20 relative to the body portion 11 causes the relatively large externally threaded region 26 of the tip portion 20 to cooperate with the relatively large internally threaded region 16 of the bore provided in the second end of the body portion 11, as shown in FIG. 2. When the relatively large externally threaded region 26 of the tip portion 20 cooperates with the relatively large internally threaded region 16 of the bore, the tip portion 20 is supported at an extended position relative to the body portion 11. In this extended position, the tip portion 20 is extended beyond the cutting tip 14 of the second end of the body portion 11. The purpose for supporting the tip portion 20 in this extended position relative to the body portion 11 will be explained below.

Figure 3:
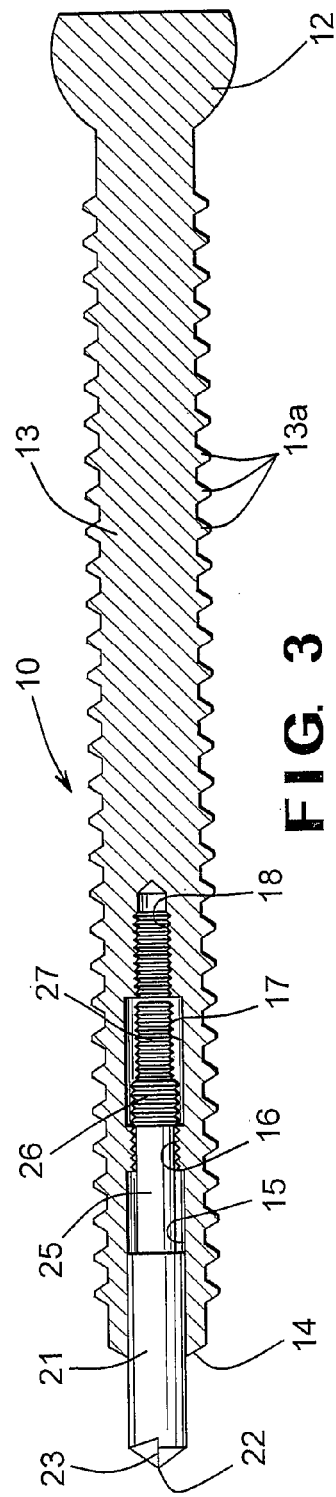
FIG. 3 is an assembled side elevational view, partially in cross section, of the first embodiment of the pedicle screw assembly illustrated in FIG. 1, wherein the tip portion is shown in an intermediate position relative to the body portion.

Further rotation of the tip portion 20 relative to the body portion 11 causes the tip portion 20 to be withdrawn within the bore provided in the second end of the body portion 11. As shown in FIG. 3, the tip portion 20 can be moved to an intermediate position relative to the body portion 11, wherein part of the tip portion 20 is located within the second end of the body portion 11, but the drill tip cutting edge 22 and the clearance cutting edge 23 of the tip portion 20 are still extended beyond the cutting tip 14 of the second end of the body portion 11. In this intermediate position, both the relatively large externally threaded region 26 and the relatively small externally threaded region 27 of the tip portion 20 may be completely received within the second non-threaded region 17 of the bore provided in the second end of the body portion 11, although such is not required. When received in this manner, however, a relative small amount of axial sliding movement may freely occur between the tip portion 20 and the body portion 11. The purpose for supporting the tip portion 20 in this intermediate position relative to the body portion 11 will also be explained below.

Figure 4:
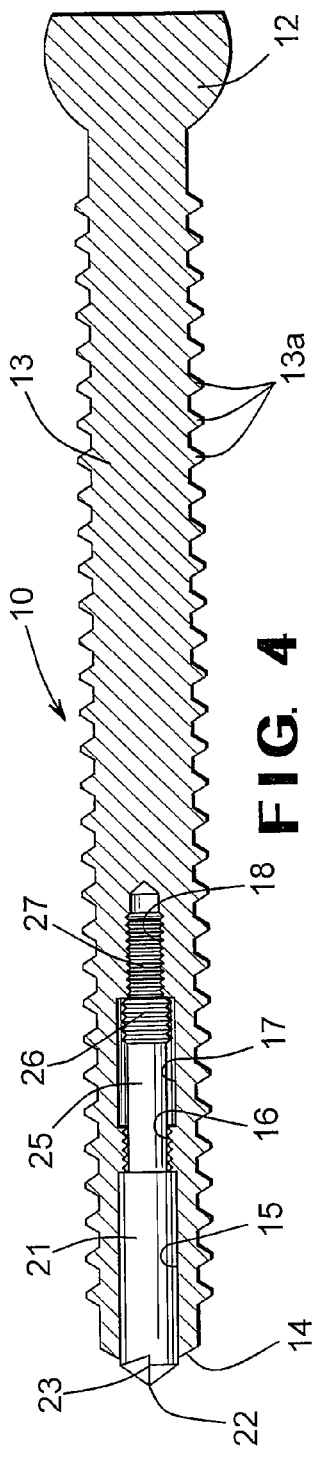
FIG. 4 is an assembled side elevational view, partially in cross section, of the first embodiment of the pedicle screw assembly illustrated in FIG. 1, wherein the tip portion is shown in a retracted position relative to the body portion.

The outer diameter defined by the relatively small externally threaded region 27 of the tip portion 20 is approximately the same as the inner diameter defined by the relatively small internally threaded region 18 of the bore provided in the second end of the body portion 11. Thus, as shown FIG. 4, the relatively small externally threaded region 27 of the tip portion 20 will engage the relatively small internally threaded region 18 of the bore provided in the second end of the body portion 11. Thereafter, rotation of the tip portion 20 relative to the body portion 11 causes the relatively small externally threaded region 27 of the tip portion 20 to cooperate with the relatively small internally threaded region 18 of the bore provided in the second end of the body portion 11. Thus, as shown in FIG. 4, the tip portion 20 can be supported at a retracted position relative to the body portion 11. In this retracted position, the drill tip cutting edge 22 and the clearance cutting edge 23 of the tip portion 20 are aligned with the cutting tip 14 of the second end of the body portion 11 to provide a complete drill tip. Alternatively, in this retracted position, the drill tip cutting edge 22 and the clearance cutting edge 23 of the tip portion 20 may be completely retracted within the cutting tip 14 of the second end of the body portion 11. The purpose for supporting the tip portion 20 in this retracted position relative to the body portion 11 will be explained below.

As mentioned above, many orthopedic and other surgical procedures involve the securement of a pedicle screw or a similar fastener into a bone, such as a vertebra that is located in the lumbar or thoracic regions of the spine. The pedicle screw assembly 10 of this invention provides a mechanism for facilitating the securement of a pedicle screw to a vertebra that involves a substantially lesser number of steps than is known in the art. To accomplish this, the tip portion 20 of the pedicle screw assembly 10 is pre-assembled onto the body portion 11 in the extended position illustrated in FIG. 2, as described above. Then, using any desired tool, the pedicle screw assembly 10 is then inserted through a relatively small incision until the drill tip cutting edge 22 of the tip portion engages the surface of the desired vertebra at a location where the pedicle screw is desired to be secured. The precise location where the drill tip cutting edge 22 engages the surface of the vertebra can be determined using conventional fluoroscopic or other imaging or navigational techniques.

Once the drill tip cutting edge 22 has been located at a desired location on the surface of the vertebra, the pedicle screw assembly 10 is then advanced further within a pedicle portion of the vertebra, such as by using a conventional impaction tool (see FIG. 18) so as to create a hole in the vertebra. During the use of this impaction tool, the relatively large externally threaded region 26 of the tip portion 20 cooperates with the relatively large internally threaded region 16 of the bore. The cooperation of these relatively large internally and externally threaded regions 16 and 26 provide sufficient strength to endure the impact forces created by the impaction tool.

The extended tip portion 20 of the pedicle screw assembly 10 can be guided into the pedicle of the vertebra by conventional fluoroscopic or other imaging or navigational techniques by use of appropriate impaction forces on the head 12 thereof. The ideal point for location of the tip portion 20 is just past the pedicle into the vertebral body, at which time the cutting edge 14 of the body portion 11 is resting on the external surface of the vertebra. A broad cutting surface 14 prevents further impaction and undesirable advancement of the modified tip 20 into the vertebral body. At this point, second phase of the insertion of the pedicle screw assembly 10 is begun, as described in detail below.

After the drill tip cutting edge 22 has formed the hole in the vertebra, the impaction tool is removed and the body portion 11 of the pedicle screw assembly 10 is rotated. Such rotation may be effected by means of any conventional tool (see FIG. 19). During such rotation of the body portion 11 of the pedicle screw assembly 10, the drill tip cutting edge 22 of the tip portion 20 remains stationary because of friction between it and the bone of the vertebra. Alternatively, the drill tip cutting edge 22 of the tip portion 20 remains stationary because of the non-circular cross-sectional shape of the body 21, such as by virtue of friction or the grooves 21a or other structures discussed above. In any event, the rotation of the body portion 11 of the pedicle screw assembly 10 occurs relative to the tip portion 20 thereof.

Consequently, the tip portion 20 is drawn within the bore of the body portion 11 of the pedicle screw assembly 10 until it reaches the intermediate position illustrated in FIG. 3. In this intermediate position, the relatively large externally threaded region 26 of the tip portion 20 is disengaged from the relatively large diameter internally threaded region 16 of the body portion 11. Additionally, the relatively small externally threaded region 27 of the tip portion 20 has not yet become engaged with the relatively small diameter internally threaded region 18 of the body portion 11. The provision of this intermediate position insures that the rotational movement of the tip portion 20 relative to the body portion 11 is not impeded by the simultaneous engagement of both the relatively large threaded regions 16 and 26 and the relatively small internally threaded regions 18 and 27 of the tip portion 20 and the body portion 11.

Further rotation of the body portion 11 of the pedicle screw assembly 10 relative to the tip portion 20 causes the tip portion 20 to be further withdrawn within the bore of the body portion 11 of the pedicle screw assembly 10 until it reaches the retracted position illustrated in FIG. 4. In this retracted position, the relatively small externally threaded region 27 of the tip portion 20 is engaged with the relatively small diameter internally threaded region 18 of the body portion 11. In the final retracted position, the drill tip cutting edge 22 and the clearance cutting edge 23 of the tip portion 20 are safely housed within the shank 13 of the body portion 11. Thereafter, the shank 13 of the body portion 11 can be further advanced within the vertebra to the desired depth by continued rotation. As the shank 13 of the body portion 11 is continued to be rotated, its cutting edge 14 starts cutting threads in bone. At the same time, the helical thread 13a provided on the outer surface of the shank 13 of the body portion 11 forms an internal tap within the hole formed in the vertebra. To accomplish this, the helical thread 13a provided on the outer surface of the shank 13 may have a self-tapping feature provided thereon, at least for a predetermined distance inwardly from the cutting tip 14. In its final resting position, the tip portion 20 becomes permanently housed within the shank 13 of the body portion 11 and is left within the vertebra after installation of the pedicle screw assembly 10.

It should be understood that other tip configurations, such as pyramidal, diamond, conical, spear, or any other desired shape or combination of shapes may be chosen to facilitate advancement of the tip portion 20 within the vertebra with impaction and to resist rotational forces as the body portion 11 is advanced over the tip portion 20. Also, the tip portion 20 may be formed having different diameters. In general, a smaller diameter pedicle screw assembly 10 will have a tip portion 20 with reduced diameter, as compared with a thicker diameter pedicle screw assembly. The thread length, pitch, and other attributes of both the relatively large diameter externally threaded region 26 and the relatively small diameter externally threaded region 27 may also vary to ensure retention of the tip portion in the extended position during the initial impaction process and to ensure movement of the tip portion 20 to the retracted position as the body portion 11 is advanced over the tip portion 20 during the rotation thereof, as described above. In the extended position, the tip portion 20 may extend any desired distance from the cutting tip 14, such as in the range of from about five millimeters to about twenty-five millimeters for example. Typically, a shorter length (such as is usually necessary in thoracic spine or patients with smaller vertebrae) would require the tip portion 20 to be projecting out of the body portion 11 for a shorter distance in the extended position. Conversely, longer extensions of the tip portion 20 would be desirable for use in lumbar spine and in patients with bigger vertebrae.

Figure 5:
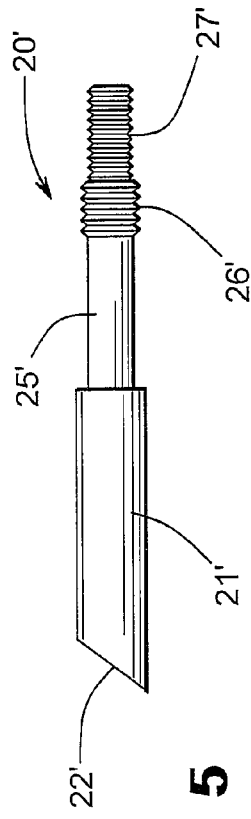
FIG. 5 is a side elevational view of a modified tip portion that can be used with the pedicle screw assembly of this invention.

FIG. 5 illustrates a modified tip portion, indicated generally at 20', that can be used with the pedicle screw assembly 10 of this invention. The modified tip portion 20' is similar to the tip portion 20 described above, and like reference numbers are used to indicate similar parts. The modified tip portion 20' is embodied as a beveled tip having a body 21' that includes a beveled tip edge 22'. An elongated shank 25' extends from the body 21' and has both a relatively large diameter externally threaded region 26' and a relatively small diameter externally threaded region 27' provided thereon. The modified tip portion 20' cooperates with the body portion 11 of the pedicle screw assembly 10 in the same general manner as described above, being movable between extended, intermediate, and retracted positions.

Figure 6:
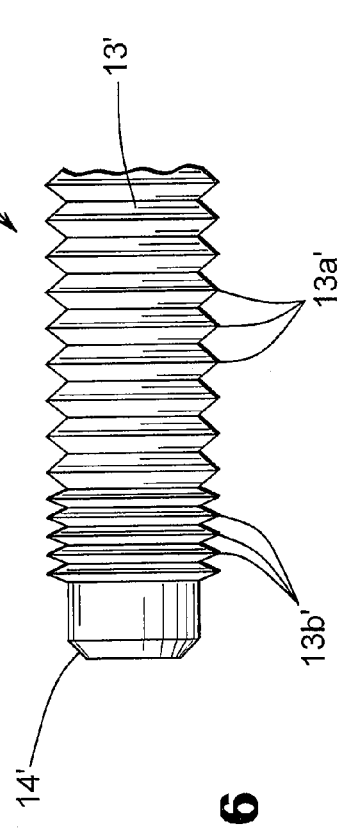
FIG. 6 is a side elevational view of a portion of a first modified body portion that can be used with the pedicle screw assembly of this invention.

FIG. 6 illustrates a portion of a first modified body portion, indicated generally at 11', that can be used with the pedicle screw assembly 10 of this invention. The first modified body portion 11' is similar to the body portion 11 described above, and like reference numbers are used to indicate similar parts. The first modified body portion 11' includes a head (not shown) provided at a first end thereof and an elongated shank 13' that extends from the head portion and terminates in a cutting tip 14'. The shank 13' of the first modified body portion 11' has an outer surface that is provided with a helical or similar thread 13a'. Additionally, however, the helical thread 13a' has a relatively fine pitch lead portion 13b'. Such lead portion 13b' of the thread 13a' initially engages the pedicle of the vertebra when the first modified body portion 11' is initially rotated relative thereto and can assist in providing precise control of the retraction of the tip portion 20 within the shank 13'. A significant differential in the pitch of the relatively large diameter externally threaded region 26 and the relatively small diameter externally threaded region 27 on the tip portion 20 and the thread 13' on the first modified body portion 11' may lead to internal binding and friction at the interface between the two components, causing an undesirable continued advancement of the modified tip portion 20 anteriorly with penetration of the anterior vertebral cortex. This dual thread portion formed with a relatively fine pitch 13b' closer to the pitch of the relatively large diameter externally threaded region 26 and the relatively small diameter externally threaded region 27 of the modified screw tip 20 will ensure reliable retraction of the tip portion 20 within the shank 13'. Thereafter, the normal helical thread 13a' of the first modified body portion 11' with a higher lead would facilitate a faster insertion of the remainder of the shank 13'.

Figure 7:
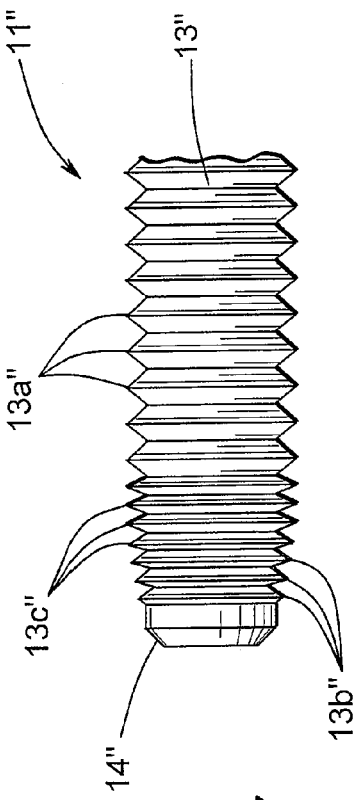
FIG. 7 is a side elevational view of a portion of a second modified body portion that can be used with the pedicle screw assembly of this invention.

FIG. 7 illustrates a portion of a second modified body portion, indicated generally at 11'', that can be used with the pedicle screw assembly 10 of this invention. The second modified body portion 11'' is also similar to the first modified body portion 11' described above, and like reference numbers are used to indicate similar parts. The second modified body portion 11'' includes a head (not shown) provided at a first end thereof and an elongated shank 13'' that extends from the head portion and terminates in a cutting tip 14''. The shank 13'' of the second modified body portion 11'' has an outer surface that is provided with a helical or similar thread 13a''. Additionally, however, the helical thread 13a'' has a relatively fine pitch lead portion 13b''. Such lead portion 13b'' of the thread 13a'' initially engages the pedicle of the vertebra when the first modified body portion 11'' is initially rotated relative thereto and can assist in providing precise control of the retraction of the tip portion 20 within the shank 13'' as described above. Furthermore, a tapered or conical transition portion 13c'' is provided between the helical thread 13a'' and the lead portion 13b'' thereof. Otherwise, the second modified body portion 11'' functions similarly to the first modified body portion 11'.

Figure 8:
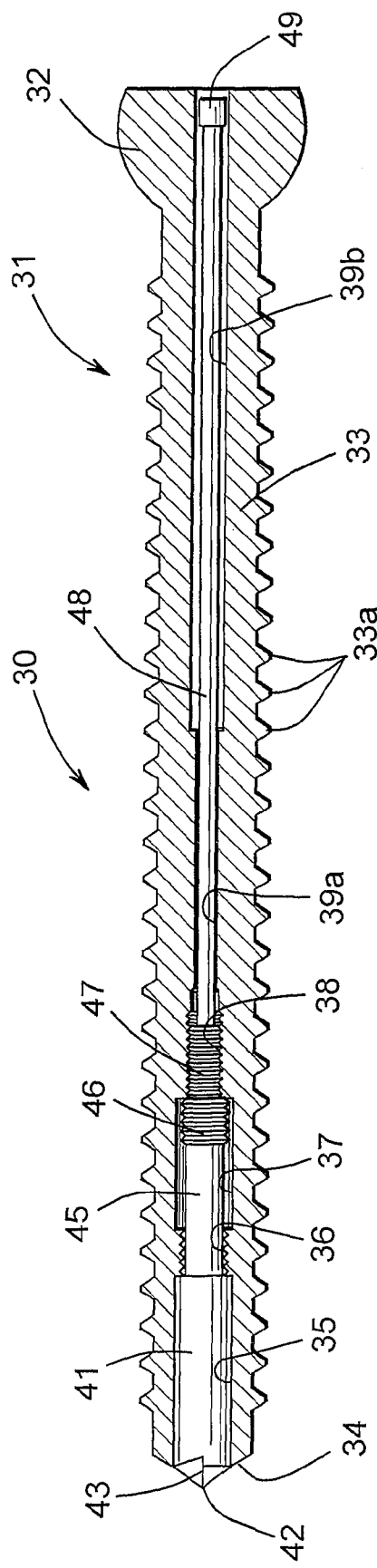
FIG. 8 is an assembled side elevational view, partially in cross section, of a second embodiment of a pedicle screw assembly in accordance with this invention.
Figure 9:
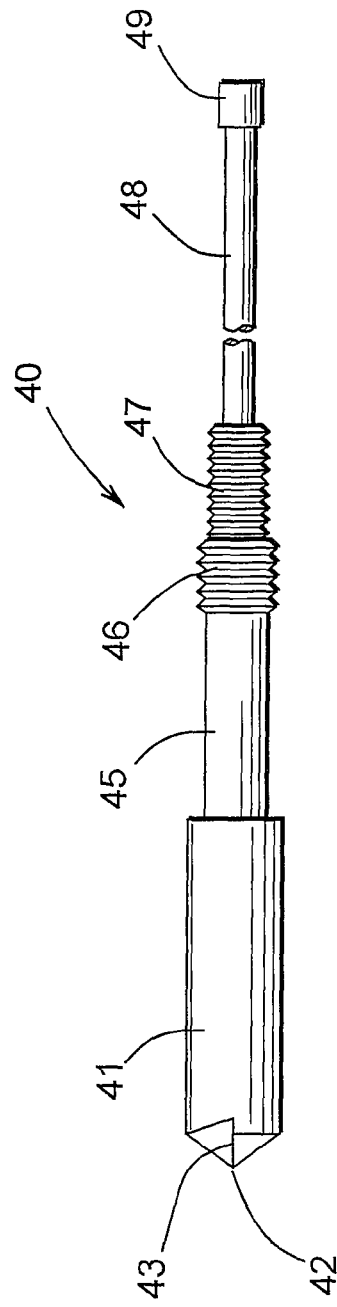
FIG. 9 is an enlarged side elevational view of a tip portion of the second embodiment of the pedicle screw assembly illustrated in FIG. 8.

FIGS. 8 and 9 illustrate a second embodiment of a pedicle screw assembly, indicated generally at 30, in accordance with this invention. The second embodiment of the pedicle screw assembly 30 includes a body portion, indicated generally at 31, having a head 32 provided at a first end thereof and an elongated shank 33 that extends from the head portion 32. The shank 33 of the body portion 31 has an outer surface that is provided with a helical or similar thread 33a. The body portion 31 of the second embodiment of the pedicle screw assembly 30 has a second end that terminates in a cutting tip 34. The second end of the body portion 31 also has a bore provided therein that extends inwardly from the cutting tip 34, including a first non-threaded region 35, a relatively large diameter internally threaded region 36, a second non-threaded region 37, and a relatively small diameter internally threaded region 38. In this second embodiment of the pedicle screw assembly 30, however, the bore continues completely through the body portion 31. In the illustrated embodiment, this through bore includes a reduced diameter portion 39a that extends from the relatively small diameter internally threaded region 38 and an enlarged diameter portion 39b that extends from the reduced diameter portion 39a.

The second embodiment of the pedicle screw assembly 30 also includes a tip portion, indicated generally at 40. In this second embodiment of the pedicle screw assembly 30, the tip portion 40 is embodied as a self-drilling tip having a body 41 that includes a drill tip cutting edge 42 and a clearance cutting edge 43. However, the tip portion 40 may alternatively include a beveled tip that includes a beveled tip edge, such as shown in FIG. 5, or any other desired shape or structure as discussed above. An elongated shank 45 extends from the body 41 and has both a relatively large diameter externally threaded region 46 and a relatively small diameter externally threaded region 47 provided thereon.

In this second embodiment of the pedicle screw assembly 30, however, the tip portion 40 additionally includes an elongated extension 48 that terminates in an enlarged end 49. The enlarged end 49 defines an outer diameter that is larger than the reduced diameter portion 39a of the bore formed through the body portion 41, but is smaller than the enlarged diameter portion 39b of such bore. To assemble the second embodiment of the pedicle screw assembly 30, the tip portion 40 is initially provided in two separate parts, namely, a first part including the body 41, the shank 45, and the externally threaded regions 46 and 47 and a second part including the elongated extension 48 and the enlarged end 49. The first part of the tip portion 40 can be installed within the body portion 30 in the same manner as described above. Thereafter, the elongated extension 48 can be secured to the shank 45 of the tip portion 40 by any desired means. For example, the elongated extension 48 can be secured to the shank 45 by press fitting, welding, threading, adhesive, and the like. Alternatively, the second embodiment of the modified screw assembly 30 may be assembled as follows. The tip portion 40 is initially provided in two separate parts, namely, a first part (including the body 41, the shank 45, and the externally threaded regions 46 and 47 as well as the elongated extension 48) and a second part (including only the enlarged end 49). The first part of the tip portion 40 can be installed within the body portion 30 in the same manner as described above. Thereafter, the enlarged end 49 can be secured to the elongated extension 48 of the tip portion 40 by any desired means, such as by press fitting, welding, threading, adhesive, and the like. Regardless, when so secured, the enlarged end 49 functions as a stop to positively prevent the tip portion 40 of the second embodiment of the pedicle screw assembly 30 from being removed from the body portion 31 thereof. Otherwise, the second embodiment of the pedicle screw assembly 30 functions in a manner similar to the first embodiment of the pedicle screw assembly 10 described above.

Figure 10:
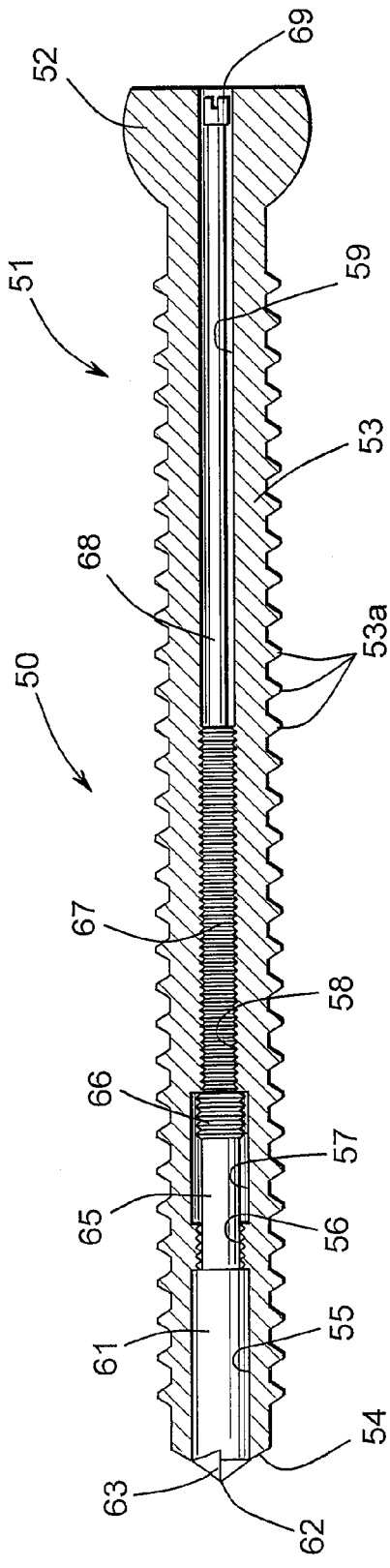
FIG. 10 is an assembled side elevational view, partially in cross section, of a third embodiment of a pedicle screw assembly in accordance with this invention.
Figure 11:
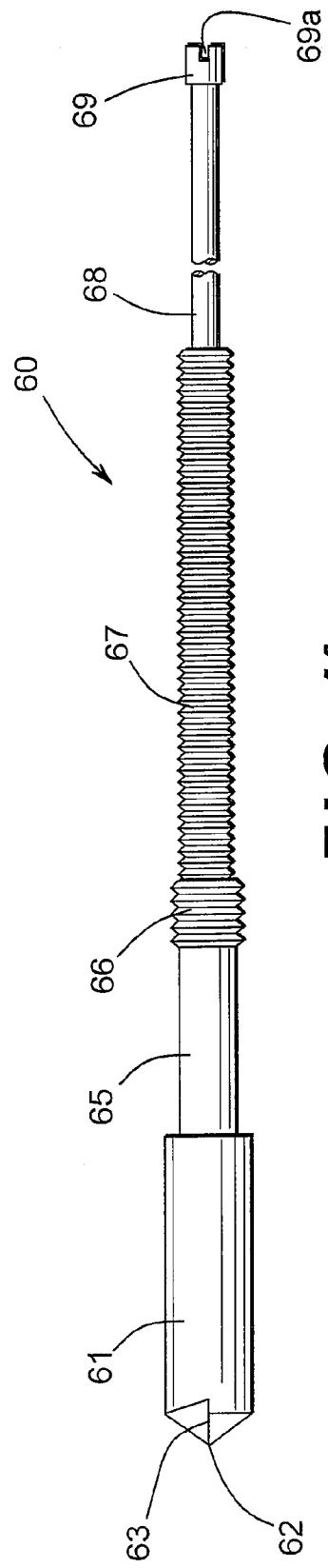
FIG. 11 is an enlarged side elevational view of a tip portion of the third embodiment of the pedicle screw assembly illustrated in FIG. 10.

FIGS. 10 and 11 illustrate a third embodiment of a pedicle screw assembly, indicated generally at 50, in accordance with this invention. The third embodiment of the pedicle screw assembly 50 includes a body portion, indicated generally at 51, having a head 52 provided at a first end thereof and an elongated shank 53 that extends from the head portion 52. The shank 53 of the body portion 51 has an outer surface that is provided with a helical or similar thread 53a. The body portion 51 of the third embodiment of the pedicle screw assembly 50 has a second end that terminates in a cutting tip 54. The second end of the body portion 51 also has a bore provided therein that extends inwardly from the cutting tip 54, including a first non-threaded region 55, a relatively large diameter internally threaded region 56, a second non-threaded region 57, and a relatively small diameter internally threaded region 58. In this third embodiment of the pedicle screw assembly 50, however, the bore 59 continues completely through the body portion 51.

The third embodiment of the pedicle screw assembly 50 also includes a tip portion, indicated generally at 60. In this third embodiment of the pedicle screw assembly 50, the tip portion 60 is embodied as a self-drilling tip having a body 61 that includes a drill tip cutting edge 62 and a clearance cutting edge 63. However, the tip portion 60 may alternatively include a beveled tip that includes a beveled tip edge, such as shown in FIG. 5, or any other desired structure as discussed above. An elongated shank 65 extends from the body 41 and has both a relatively large diameter externally threaded region 66 and a relatively small diameter externally threaded region 67 provided thereon.

In this third embodiment of the pedicle screw assembly 50, however, the relatively small externally threaded region 67 extends axially further along the tip portion 60 than in the previous embodiments. Specifically, the axial length of the relatively small externally threaded region 67 is sufficiently long that when the tip portion 60 is initially inserted within the body portion 51, the relatively small externally threaded region 67 engages the relatively small internally threaded region 58 provided within the bore of the body portion 51. Thus, further rotation of the tip portion 60 is necessary for the relatively large externally threaded region 66 to engage the relatively large internally threaded region 56 of the body portion 51 and thereby locate the tip portion 60. This extended axial length of the relatively small externally threaded region 67 insures that the tip portion 60 is always threaded into the body portion 51 to positively prevent the tip portion 60 of the second embodiment of the pedicle screw assembly 50 from being removed from the body portion 31 thereof.

The tip portion 60 additionally includes an elongated extension 68 that terminates in an end 69. The end 69 has a drive mechanism provided therein that is adapted to cooperate with a conventional rotation tool (see FIG. 19) to effect rotation of the tip portion 60 relative to the body portion 51. In the illustrated embodiment, the drive mechanism is a slot 69*a* that can cooperate with a conventional flat-head screwdriver. However, the drive mechanism can be embodied as any conventional structure for accomplishing this purpose. The elongated extension 68 and the end 69 can be formed integrally with the remainder of the tip portion 61 or can be formed separately and secured thereto, as described above. Otherwise, the third embodiment of the pedicle screw assembly 50 functions in a manner similar to the embodiments of the pedicle screw assembly 10 and 30 described above.

Figure 12:
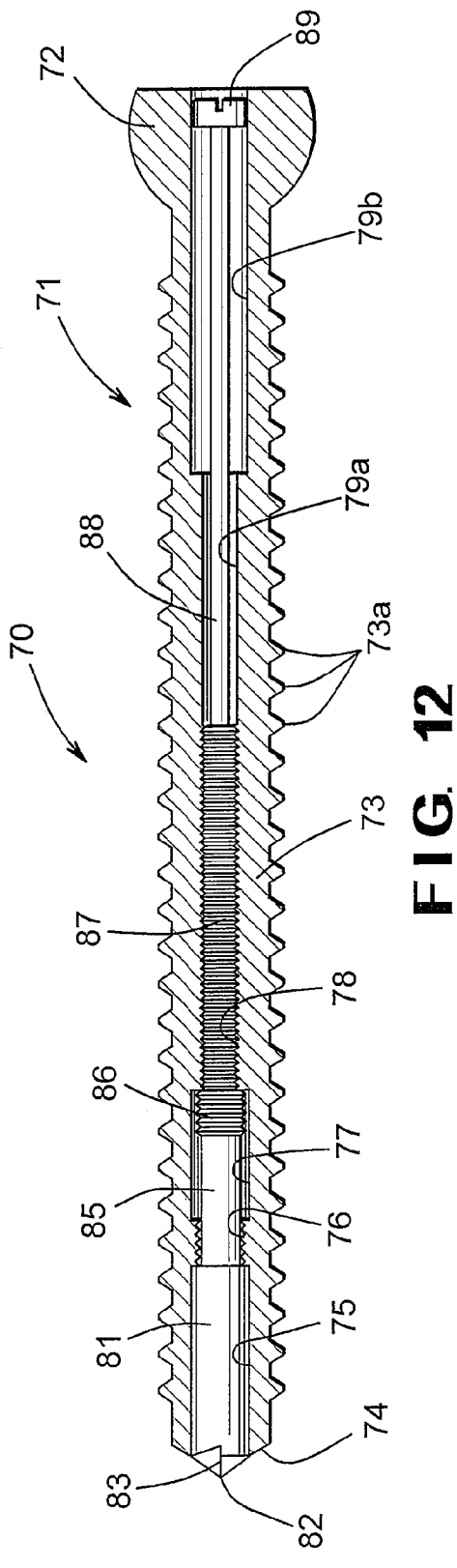
FIG. 12 is an assembled side elevational view, partially in cross section, of a fourth embodiment of a pedicle screw assembly in accordance with this invention.
Figure 13:
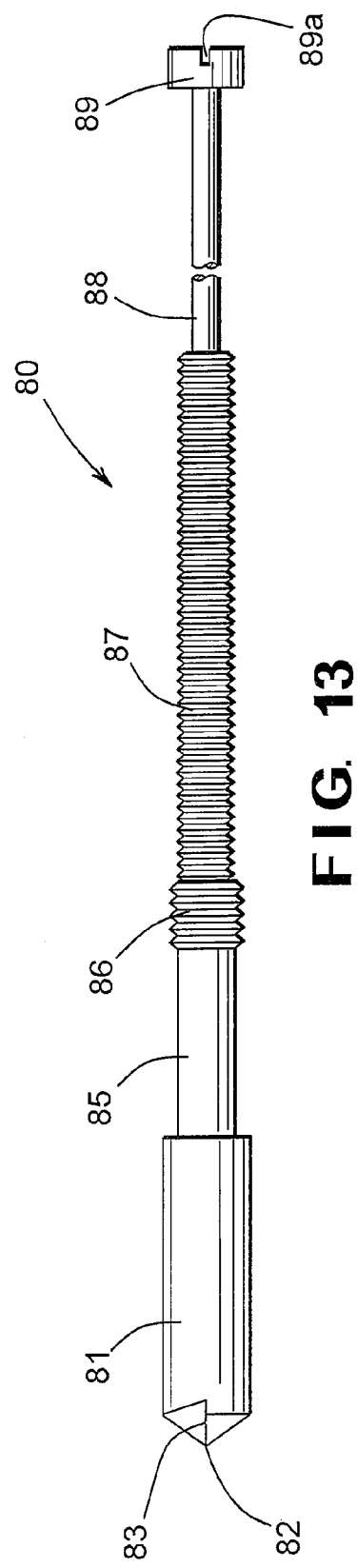
FIG. 13 is an enlarged side elevational view of a tip portion of the fourth embodiment of the pedicle screw assembly illustrated in FIG. 12.

FIGS. 12 and 13 illustrate a fourth embodiment of a pedicle screw assembly, indicated generally at 70, in accordance with this invention. The fourth embodiment of the pedicle screw assembly 70 includes a body portion, indicated generally at 71, having a head 72 provided at a first end thereof and an elongated shank 73 that extends from the head portion 72. The shank 73 of the body portion 71 has an outer surface that is provided with a helical or similar thread 73*a*. The body portion 71 of the fourth embodiment of the pedicle screw assembly 70 has a second end that terminates in a cutting tip 74. The second end of the body portion 71 also has a bore provided therein that that extends inwardly from the cutting tip 74, including a first non-threaded region 75, a relatively large diameter internally threaded region 76, a second non-threaded region 77, and a relatively small diameter internally threaded region 78. In this fourth embodiment of the pedicle screw assembly 70, however, the bore continues completely through the body portion 71. In the illustrated embodiment, this through bore includes a reduced diameter portion 79*a* that extends from the relatively small diameter internally threaded region 78 and an enlarged diameter portion 79*b* that extends from the reduced diameter portion 79*a*.

The fourth embodiment of the pedicle screw assembly 70 also includes a tip portion, indicated generally at 80. In this fourth embodiment of the pedicle screw assembly 70, the tip portion 80 is embodied as a self-drilling tip having a body 81 that includes a drill tip cutting edge 82 and a clearance cutting edge 83. However, the tip portion 80 may alternatively include a beveled tip that includes a beveled tip edge, such as shown in FIG. 5, or any other desired structure as described above. An elongated shank 85 extends from the body 81 and has both a relatively large diameter externally threaded region 86 and a relatively small diameter externally threaded region 87 provided thereon.

In this fourth embodiment of the pedicle screw assembly 70, however, the tip portion 80 additionally includes an elongated extension 88 that terminates in an enlarged end 89. The enlarged end 89 defines an outer diameter that is larger than the reduced diameter portion 79*a* of the bore formed through the body portion 71, but is smaller than the enlarged diameter portion 79*b* of such bore. Additionally, the enlarged end 89 has a drive mechanism provided therein that is adapted to cooperate with a conventional rotation tool (see FIG. 19) to effect rotation of the tip portion 80 relative to the body portion 71. In the illustrated embodiment, the drive mechanism is a slot 89*a* that can cooperate with a conventional flat-head screwdriver. However, the drive mechanism can be embodied as any conventional threaded or non-threaded structure for accomplishing this purpose. The elongated extension 88 and the end 89 can be formed integrally with the remainder of the tip portion 81 or can be formed separately and secured thereto, as described above. Otherwise, the fourth embodiment of the pedicle screw assembly 70 functions in a manner similar to the embodiments of the pedicle screw assembly 10, 30, and 50 described above.

FIG. 14 illustrates a fifth embodiment of a pedicle screw assembly, indicated generally at 70', in accordance with this invention. The fifth embodiment of the pedicle screw assembly 70' is similar to the fourth embodiment 70 described above, and like reference numbers are used to indicate similar parts. In this fifth embodiment of the pedicle screw assembly 70', however, the second non-threaded region 77' of the body portion 81' has an extended non-threaded region 77*a*' provided thereon. Similarly, an extended non-threaded region 86*a*' is provided between the relatively large externally threaded region 86' and the relatively small externally threaded region 87' provided on the tip portion 81'. The extended non-threaded regions 77*a*' and 86*a*' are provided to facilitate the installation of the tip portion 80' within the bore of the body portion 71'. Otherwise, the fifth embodiment of the pedicle screw assembly 70' functions in a manner similar to the fourth embodiment of the pedicle screw assembly 70 described above.

FIG. 15 illustrates a sixth embodiment of a pedicle screw assembly, indicated generally at 70", in accordance with this invention. The sixth embodiment of the pedicle screw assembly 70" is similar to the fifth embodiment 70' described above, and like reference numbers are used to indicate similar parts. In this sixth embodiment of the pedicle screw assembly 70", however, the thread 73*a*" provided outer surface of the shank 73" of the body portion 71" has an enlarged diameter region 73*b*" located adjacent to the head 72". The enlarged diameter region 73*b*" of the thread 73" is provided to increase the diameter of the hole formed in the vertebra adjacent to the surface thereof, which would allow the use of a pedicle screw having a correspondingly larger diameter threaded portion, thereby increasing the strength of the connection between the pedicle screw and the vertebra. Otherwise, the sixth embodiment of the pedicle screw assembly 70' functions in a manner similar to the fifth embodiment of the pedicle screw assembly 70 described above.

Figure 16:
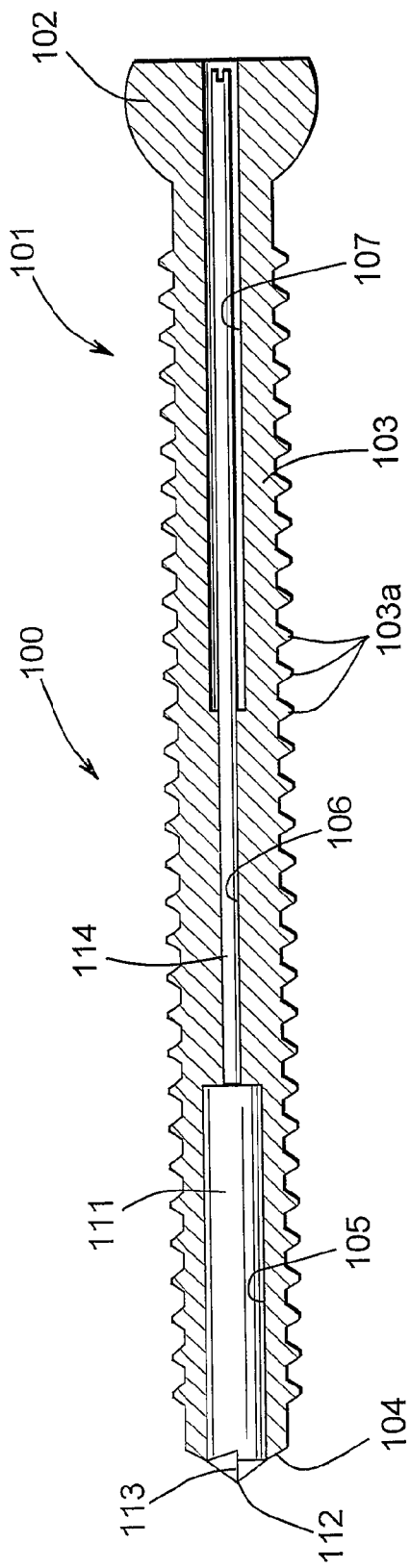
FIG. 16 is an assembled side elevational view, partially in cross section, of a seventh embodiment of a pedicle screw assembly in accordance with this invention.
Figure 17:
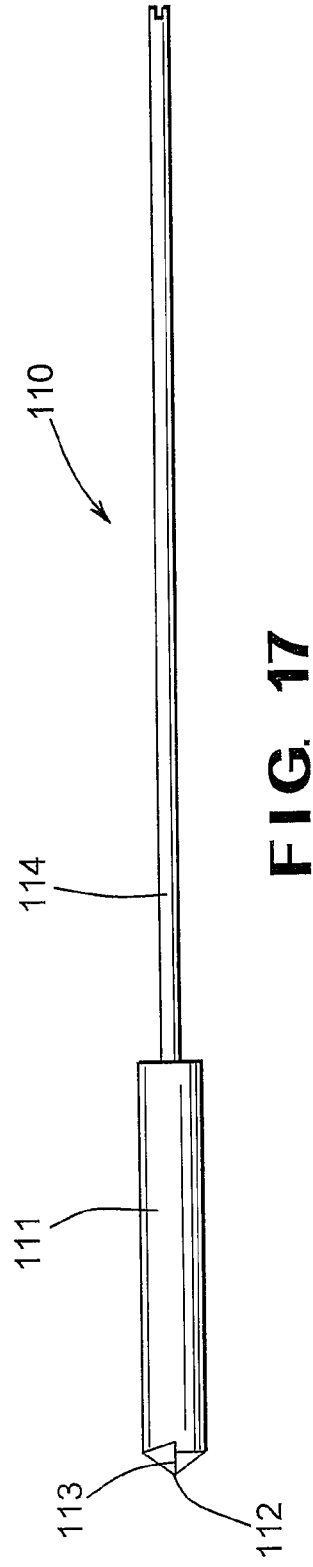
FIG. 17 is a sectional elevational view of a tip portion of the seventh embodiment of the pedicle screw assembly illustrated in FIG. 16.

FIGS. 16 and 17 illustrate a seventh embodiment of a pedicle screw assembly, indicated generally at 100, in accordance with this invention. The seventh embodiment of the pedicle screw assembly 100 includes a body portion, indicated generally at 101, having a head 102 provided at a first end thereof and an elongated shank 103 that extends from the head portion 102. The shank 103 of the body portion 101 has an outer surface that is provided with a helical or similar thread 103*a*. The body portion 101 of the seventh embodiment of the pedicle screw assembly 100 has a second end that terminates in a cutting tip 104. The second end of the body portion 101 also has a bore provided therein that that extends inwardly from the cutting tip 104, including a first non-threaded region 105, an internally threaded region 106, and a second non-threaded region 107. In this seventh embodiment of the pedicle screw assembly 100, however, the bore continues completely through the body portion 101. In the illustrated embodiment, the first non-threaded region 105 defines a smaller internal diameter than the second non-threaded region 107. However, such is not required.

The seventh embodiment of the pedicle screw assembly 100 also includes a tip portion, indicated generally at 110. In this seventh embodiment of the pedicle screw assembly 100, the tip portion 110 is embodied as a self-drilling tip having a body 111 that includes a drill tip cutting edge 112 and a clearance cutting edge 113. However, the tip portion 110 may alternatively include a beveled tip that includes a beveled tip edge, such as shown in FIG. 5, or any other desired structure as discussed above. An elongated shank 114 extends from the body 111 and is externally threaded throughout. The externally threaded elongated shank 114 cooperates with the internally threaded region 106 of the bore formed through the body portion 101. Otherwise, the seventh embodiment of the pedicle screw assembly 100 functions in a manner similar to the embodiments of the pedicle screw assembly described above.

Figure 18:
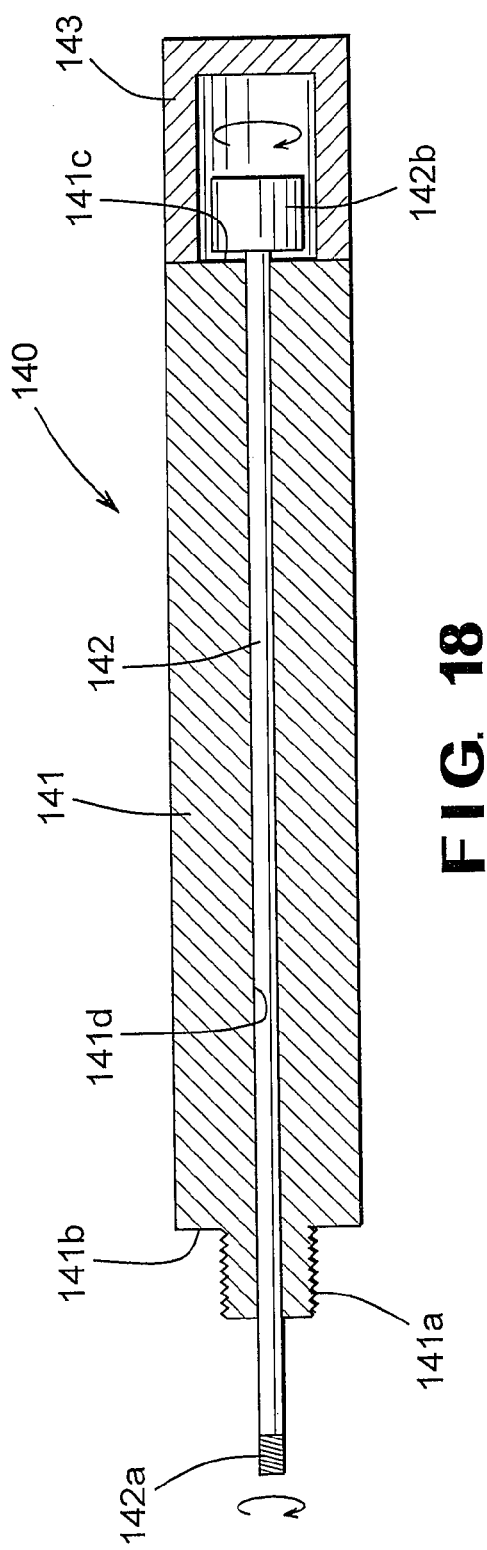
FIG. 18 is a side elevational view, partially in cross section, of an installation tool as used as an impaction tool in connection with the embodiments of the pedicle screw assembly described above.
Figure 19:
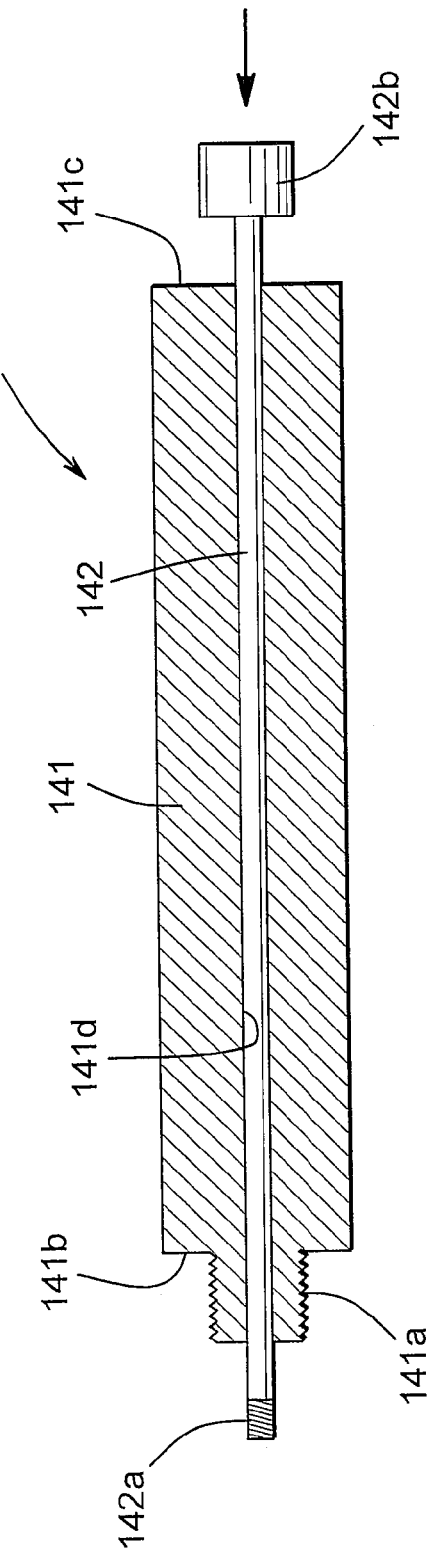
FIG. 19 is a side elevational view similar to FIG. 18 showing the installation tool as used as a rotation tool in connection with some of the embodiments of the pedicle screw assembly described above.

FIGS. 18 and 19 schematically illustrate an installation tool, indicated generally at 140, that can be used in connection with the various embodiments of the pedicle screw assembly described above. As will be explained in detail below, the installation tool 140 can function both as an impaction tool (which is used to advance the extended tip portion of the pedicle screw assembly within the pedicle of the vertebra) and as a rotation tool (which is used to effect rotation of the tip portion of the pedicle screw assembly relative to the body portion).

The illustrated installation tool 140 includes an elongated hollow body 141 having a first end and a second end. The first end of the body 141 has an externally threaded portion 141a that extends from an engagement surface 141b. The second end of the body 141 has an impaction surface 141c. A passageway 141d extends through the body 141 of the installation tool 140 from the externally threaded portion 141a to the impaction surface 141c. The externally threaded portion 141a of the body 141 is preferably sized and shaped to cooperate with the internal thread 12b provided on the tulip 12a of the pedicle screw assembly 10. The purpose for this cooperation will be explained below.

The illustrated installation tool 140 also includes a rotation tool 142 that is supported within the passageway 141d of the installation tool 140 for rotation relative to the body 141. The rotation tool 142 includes a drive portion 142a that extends outwardly from the externally threaded portion 141a at the first end of the body 141 and a head portion 142b that extends outwardly from the impaction surface 141c at the second end of the body 141. The drive portion 142a of the rotation tool 142 is preferably sized and shaped to cooperate with the drive mechanism provided on the tip portions illustrated in FIGS. 10 through 17. The purpose for this cooperation will also be explained below. Lastly, the illustrated installation tool 140 includes an impaction cap 143 that sized and shaped to fit over the head portion 142b of the rotation tool 142 and to engage the impaction surface 141c of the body 141. As shown in FIG. 18, an axial clearance is provided between the head portion 142b of the rotation tool 142 and the inner surface of the impaction cap 143. The purpose of the impaction cap 143 and this axial clearance will also be explained below.

The illustrated installation tool 140 can be used to facilitate the installation of the pedicle screw assembly as follows. If the installation tool 140 is being to install the embodiments of the pedicle screw assembly illustrated in FIGS. 1 through 9 (which do not include a drive mechanism provided on the tip portion), then the rotation tool 142 and the impaction cap 143 can be initially removed. If, on the other hand, the installation tool 140 is being to install the embodiments of the pedicle screw assembly illustrated in FIGS. 10 through 17 (which do include a drive mechanism provided on the tip portion), then the rotation tool 142 and the impaction cap 143 can be retained as shown in FIG. 18.

In either event, the externally threaded portion 141a of the body 141 is threaded into the internal thread 12b provided on the tulip 12a of the pedicle screw assembly 10. Such threading is continued until the engagement surface 141b of the body 141 engages the outermost end of the tulip 12a. As a result of this threaded engagement, the installation tool 140 is securely connected to the pedicle screw assembly 10. Then, (if the rotation tool 142 and the impaction cap 143 are to be used), the impaction cap 143 is disposed over the head portion 142b of the rotation tool 142 and into engagement with the impaction surface 141c of the body 141. The axial clearance provided between the head portion 142b of the rotation tool 142 and the inner surface of the impaction cap 143 allows the rotation tool 142 to be retracted (either partially or completely) inwardly within the externally threaded portion 141a of the body 141. Thereafter, an impact force (represented by the arrow in FIG. 18) is applied to the impaction cap 143 so as to advance the extended tip portion of the pedicle screw assembly within the pedicle of the vertebra, as described above. The impaction cap 143 is then removed, and the drive portion 142a of the rotation tool 142 is moved into cooperation with the drive mechanism provided on the tip portions illustrated in FIGS. 10 through 17. Lastly, the rotation tool 142 is rotated (represented by the arrows in FIG. 19) by rotating the head portion 142b, such as by manual manipulation. Such rotation causes concurrent rotation of the tip portion relative to the body portion of the pedicle screw assembly. As a result, the tip portion of the pedicle screw assembly can be manually moved from the extended position to the retracted position, as also described above, to allow the final installation of the pedicle screw assembly.

The principle and mode of operation of this invention have been explained and illustrated in its preferred embodiments. However, it must be understood that this invention may be practiced otherwise than as specifically explained and illustrated without departing from its spirit or scope.

What is claimed is:

1. A pedicle screw assembly comprising:
a body portion including a head and a shank, the shank including an outer surface with a thread provided thereon, an end having a cutting tip provided thereon, and a bore extending inwardly from the end and having an internally threaded region provided therein; and
a tip portion including a body having a cutting edge and a shank extending from the body, the shank having an externally threaded region provided thereon that cooperates with the internally threaded region of the bore to permit movement of the tip portion relative to the body portion between extended and retracted positions,
wherein the internally threaded region of the bore has a first internally threaded region defined by a first diameter and a second internally threaded region defined by a second diameter that is larger than the first diameter, and
wherein the externally threaded region of the tip portion has first externally threaded region that cooperates with the first internally threaded region of the bore and a second externally threaded region that cooperates with the second internally threaded region of the bore.

2. The pedicle screw assembly defined in claim 1 wherein the bore further includes a non-threaded region that is provided between the first internally threaded region and the second internally threaded region such that the tip portion can be located relative to the body portion in an intermediate position between the extended and retracted positions.

3. The pedicle screw assembly defined in claim 1 wherein the cutting edge of the tip portion includes a drill tip cutting edge and a clearance cutting edge.

4. The pedicle screw assembly defined in claim 1 wherein the cutting edge of the tip portion includes a beveled tip edge.

5. The pedicle screw assembly defined in claim 1 wherein the thread provided on the outer surface of the body portion includes a lead portion.

6. The pedicle screw assembly defined in claim 5 wherein the thread provided on the outer surface of the body portion further includes a transition portion provided between the thread and the lead portion.

7. The pedicle screw assembly defined in claim 1 wherein the bore includes a reduced diameter portion that extends from the internally threaded region and an enlarged diameter portion that extends from the reduced diameter portion, and wherein the tip portion further includes an extension that terminates in an enlarged end defining an outer diameter that is larger than the reduced diameter portion of the bore, but is smaller than the enlarged diameter portion of such bore.

8. The pedicle screw assembly defined in claim 1 wherein the tip portion further includes an extension that terminates in an end having a drive mechanism provided thereon.

9. The pedicle screw assembly defined in claim 1 wherein the tip portion includes a non-threaded region between the second externally threaded region and the first externally threaded region.

10. The pedicle screw assembly defined in claim 1 wherein the thread provided outer surface of the shank of the body portion has an enlarged diameter region located adjacent to the head.

* * * * *